(12) United States Patent
Baynham

(10) Patent No.: US 9,763,802 B2
(45) Date of Patent: Sep. 19, 2017

(54) TRANSPEDICULAR NUCLEUS REPLACEMENT SYSTEM

(71) Applicant: Atlas Spine, Inc., Jupiter, FL (US)

(72) Inventor: Matthew G. Baynham, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 469 days.

(21) Appl. No.: 14/210,262

(22) Filed: Mar. 13, 2014

(65) Prior Publication Data

US 2014/0277468 A1 Sep. 18, 2014

Related U.S. Application Data

(60) Provisional application No. 61/784,573, filed on Mar. 14, 2013.

(51) Int. Cl.
*A61F 2/44* (2006.01)
*A61F 2/30* (2006.01)
*A61F 2/46* (2006.01)

(52) U.S. Cl.
CPC ............ *A61F 2/441* (2013.01); *A61F 2/442* (2013.01); *A61F 2/30744* (2013.01); *A61F 2/4611* (2013.01); *A61F 2002/3085* (2013.01); *A61F 2002/30563* (2013.01); *A61F 2002/30588* (2013.01); *A61F 2002/444* (2013.01)

(58) Field of Classification Search
CPC .. A61F 2002/30563; A61F 2002/30588; A61F 2002/3058; A61F 2002/444; A61F 2/30744; A61F 2/441; A61F 2/442; A61F 2/4611; F16B 31/021

USPC .......... 606/300–321, 250, 265–267, 270; 623/17.11–17.16
See application file for complete search history.

(56) References Cited

U.S. PATENT DOCUMENTS

| | | | |
|---|---|---|---|
| 6,022,350 A * | 2/2000 | Ganem | A61B 17/7059 606/272 |
| 7,789,896 B2 * | 9/2010 | Jackson | A61B 17/7032 606/266 |
| 7,905,908 B2 * | 3/2011 | Cragg | A61B 17/70 606/279 |
| 8,308,777 B2 * | 11/2012 | Assell | A61B 17/025 606/279 |
| 2005/0113919 A1 * | 5/2005 | Cragg | A61B 17/70 623/17.11 |
| 2008/0188895 A1 * | 8/2008 | Cragg | A61B 17/70 606/246 |
| 2009/0099610 A1 * | 4/2009 | Johnson | A61B 17/844 606/86 R |
| 2010/0331898 A1 * | 12/2010 | Froehlich | A61B 17/7097 606/305 |
| 2011/0040329 A1 * | 2/2011 | Ainsworth | A61B 17/70 606/246 |
| 2013/0046351 A1 * | 2/2013 | Schwappach | A61F 2/0811 606/323 |

(Continued)

*Primary Examiner* — Todd E Manahan
*Assistant Examiner* — Jessica Weiss
(74) *Attorney, Agent, or Firm* — McHale & Slavin, P.A.

(57) ABSTRACT

A cannulated screw having a resilient balloon structure capable of supporting compressive and cyclic loads. The balloon provides an artificial disc prosthesis by use of the balloon that mimics the properties of the natural disc by maintaining the intervertebral disc space through a full range of natural motion, absorbing shocks and permitting a natural range of motion.

8 Claims, 7 Drawing Sheets

(56) References Cited

U.S. PATENT DOCUMENTS

| | | | |
|---|---|---|---|
| 2013/0096634 A1* | 4/2013 | Suh .................... | A61B 17/7097 606/304 |
| 2013/0245602 A1* | 9/2013 | Sweeney ............ | A61B 17/7061 604/506 |
| 2015/0362099 A1* | 12/2015 | Aramaki ............. | F16L 19/0231 285/390 |

* cited by examiner

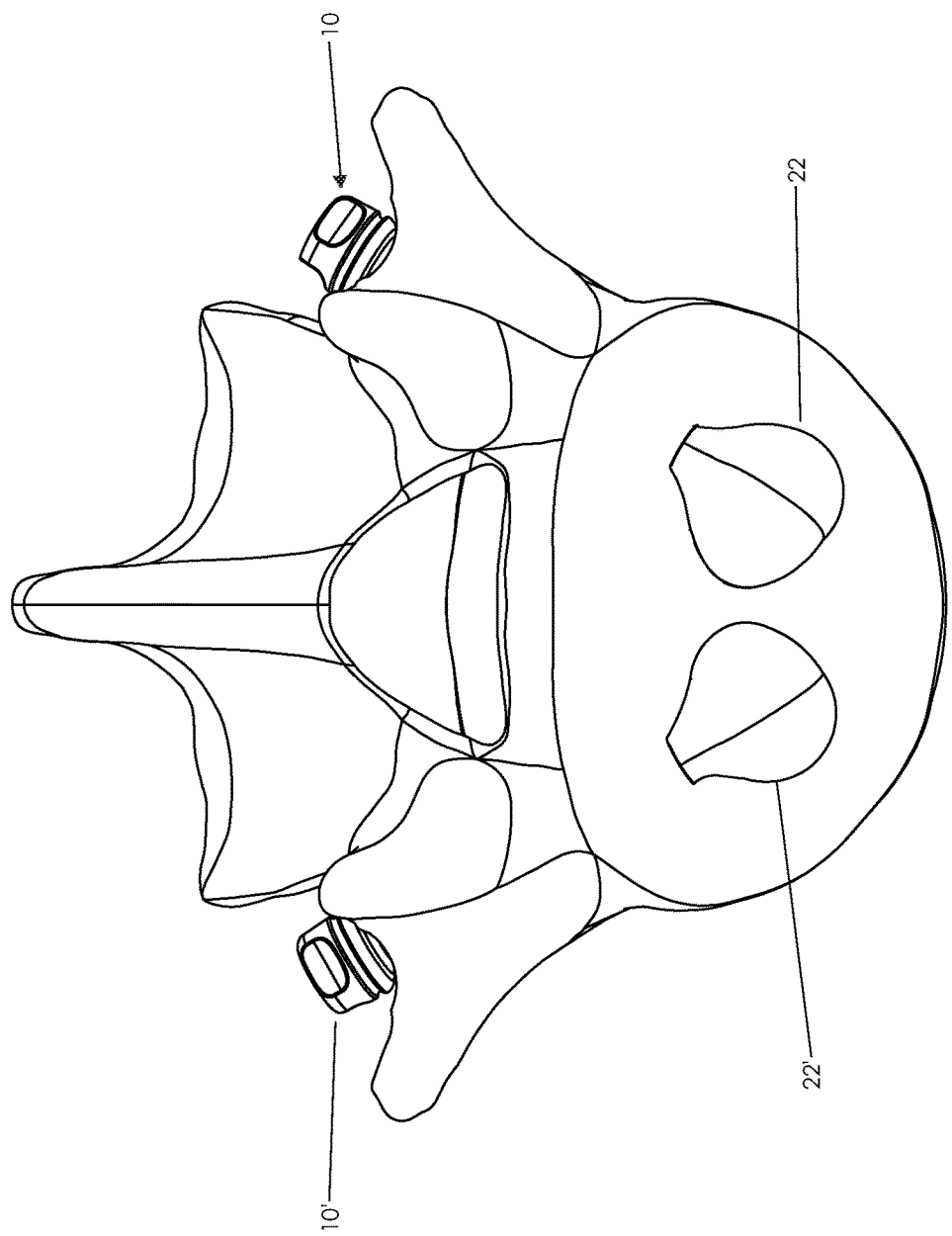

TRANSPEDICULAR NUCLEUS REPLACEMENT SYSTEM

PRIORITY CLAIM

In accordance with 37 C.F.R. 1.76, a claim of priority is included in an Application Data Sheet filed concurrently herewith. Accordingly, the present invention priority to U.S. provisional patent application Ser. No. 61/784,573, filed on Mar. 14, 2013, entitled "TRANSPEDICULAR NUCLEUS REPLACEMENT SYSTEM", the contents of which are hereby expressly incorporated herein by reference.

FIELD OF THE INVENTION

The present invention relates generally to surgically-implantable spinal devices and more specifically, to a cannulated screw with inflatable balloon.

BACKGROUND OF THE INVENTION

Intervertebral discs are oblate spherical structures that maintain the space between adjacent vertebrae. Each intervertebral disc consists of an outer annulus fibrosus, which surrounds the inner nucleus pulposus. The annulus fibrosus consists of several layers of strong annular fibrocartilage to contain the nucleus pulposus and distribute pressure evenly across the disc wherein a mucoprotein gel serves to absorb shocks.

Deterioration of an intervertebral disc results in limited mobility and can cause severe pain. For instance, normal aging causes the nucleus pulposus to lose fluid and contract in volume resulting in a reduction in the intervertebral space. Any reduction of space between adjacent vertebrae may put pressure on the nerves of the spinal column. Further, a reduction in volume of the nucleus pulposus reduces the disc's ability to absorb shock which can result in disc herniation. The bulge of a herniated disc may also put pressure on nearby nerve structures resulting in pain as well as diminished range of motion.

Surgical options are available including laminectomy and discectomy combined with vertebral fusion and/or dynamic stabilization. However, these surgical options are highly invasive and require prolonged hospitalization and recovery. More recently, artificial disc replacement prosthetics have been used to replace or augment all or part of the removed or resected intervertebral disc.

The use of an expandable balloon like artificial disc prosthesis filled with a polymer is known. A joint arthroplasty device can be formed in situ by inserting a hollow device having an aperture and a lumen into a target joint, and injecting material into the hollow device to form an implant. An artificial/prosthetic facet joint with balloon joint space component composed of latex, polymer, silicone or the like materials.

What is lacking in the field is a cannulated screw that includes an inflatable balloon to mimic the properties of the natural disc by maintaining the intervertebral disc space through a full range of natural motion and absorb the shocks of daily use.

SUMMARY OF THE INVENTION

A cannulated screw includes a resilient balloon structure capable of supporting compressive and cyclic loads. The various embodiments of the present invention may be implanted in an anterior, anterior-lateral, or a posterior surgical approach to the procedure. The size of each implant component (in collapsed form) is small enough to be inserted with minimal incisions.

Accordingly, it is an objective of the invention to provide an artificial disc prosthesis by use of a cannulated screw for inclusion of a balloon that mimics the properties of the natural disc by maintaining the intervertebral disc space through a full range of natural motion, absorbs the shocks and permits a natural range.

Another objective of the invention is to provide an artificial disc prosthesis that is anchored to the vertebral body through the pedicle.

Other objectives and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

FIG. 8 is a pictorial view illustrating the filled ballons.

DETAILED DESCRIPTION OF THE INVENTION

Figure 2:
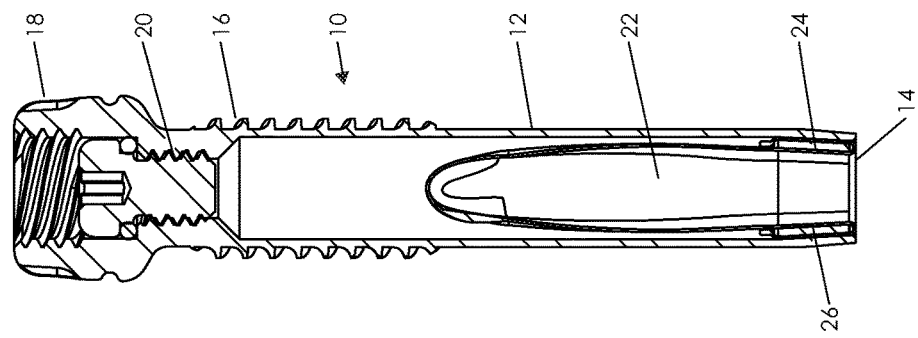
FIG. 2 is a cross sectional view thereof.

The medical device enables surgical access to the weight-bearing portion of the spine percutaneously through the pedicle. The medical device described herein comprises a cannulated screw that includes an inflatable balloon to mimic the properties of the natural disc by maintaining the intervertebral disc space through a full range of natural motion and absorb the shocks of daily use.

As such, the medical device described herein provides a better overall approach to modifying the relationship between adjacent vertebral bodies, without altering the surrounding anatomy, thereby reducing the time a patient and surgeon have to spend in surgery, and reducing or altogether eliminating hospitalization following the procedure.

Embodiments of the invention may be practiced without the theoretical aspects presented. Moreover, the theoretical aspects are presented with the understanding that Applicants do not seek to be bound by the theory presented.

It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Definitions: The terminology used herein is for the purpose of describing particular embodiments only and is not intended to be limiting of the invention. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The following description of the preferred embodiments is merely exemplary in nature and is in no way intended to limit the invention, its application or uses.

Figure 1:
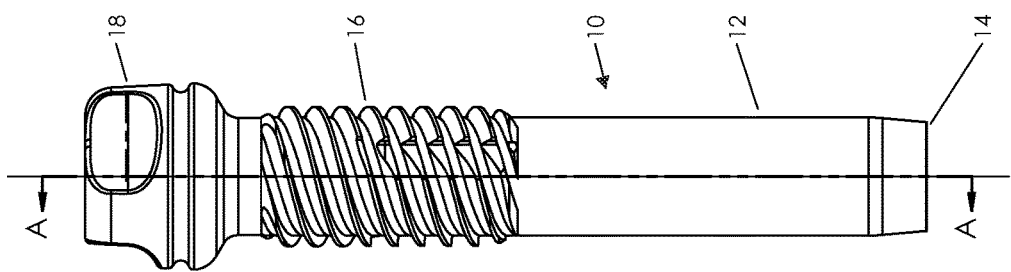
FIG. 1 is a side view of the cannulated screw of the instant invention.

FIG. 1 is a side view of the cannulated screw 10 of the instant invention. The cannulated screw 10 includes a hollow body 12 having an open end 14. An outer surface of the hollow body 12 is threaded along an upper portion 16 with a threaded cap 18 for receipt of a locking plug 20.

Figure 3:
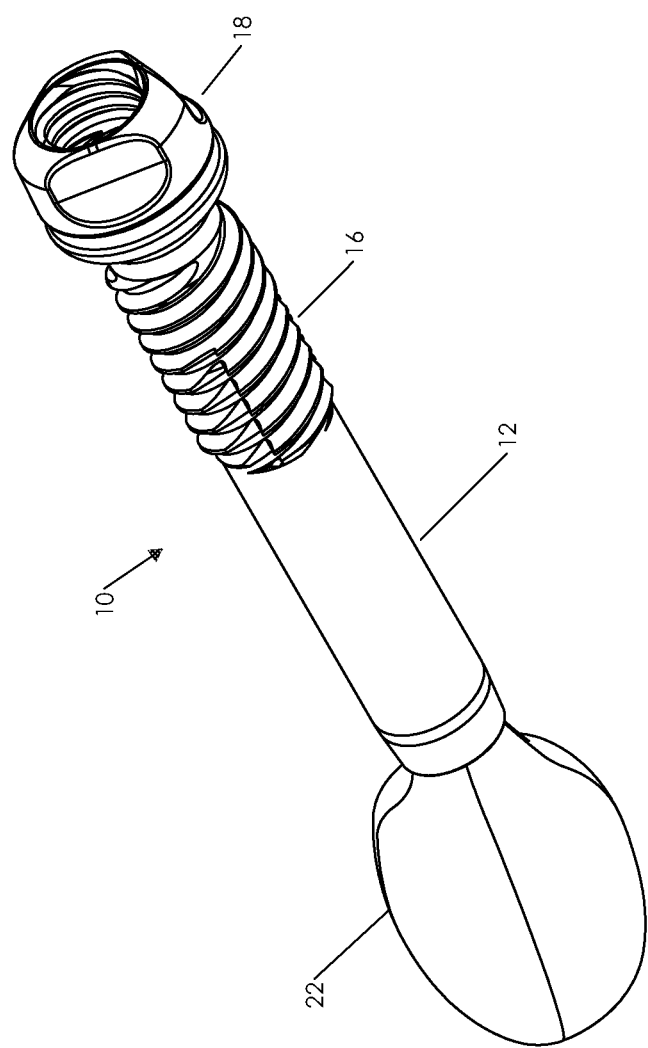
FIG. 3 is a perspective view thereof depicting the balloon in an inflated position.

FIG. 2 depicts an expandable body 22 (for example, a balloon) in a stored position. The term "balloon" will be used merely as a descriptive term, however, it is understood that any expandable body may be used. The balloon extends upward through the hollow body 12 which allows insertion through a pedicle without impacting the balloon 22. A ferrule 24 fits within an open end 26 of the balloon 22 creating a seal between the balloon and the hollow body 12. As shown in FIG. 3, the balloon is shown in an inflated position. The balloon 22 is forced to pass through the ferrule 24 further sealing the balloon 22 to the hollow body 12. Once the balloon 22 is filled with fluid, the locking plug 20 is threaded into the screw to secure the fluid within the balloon.

Figure 4:
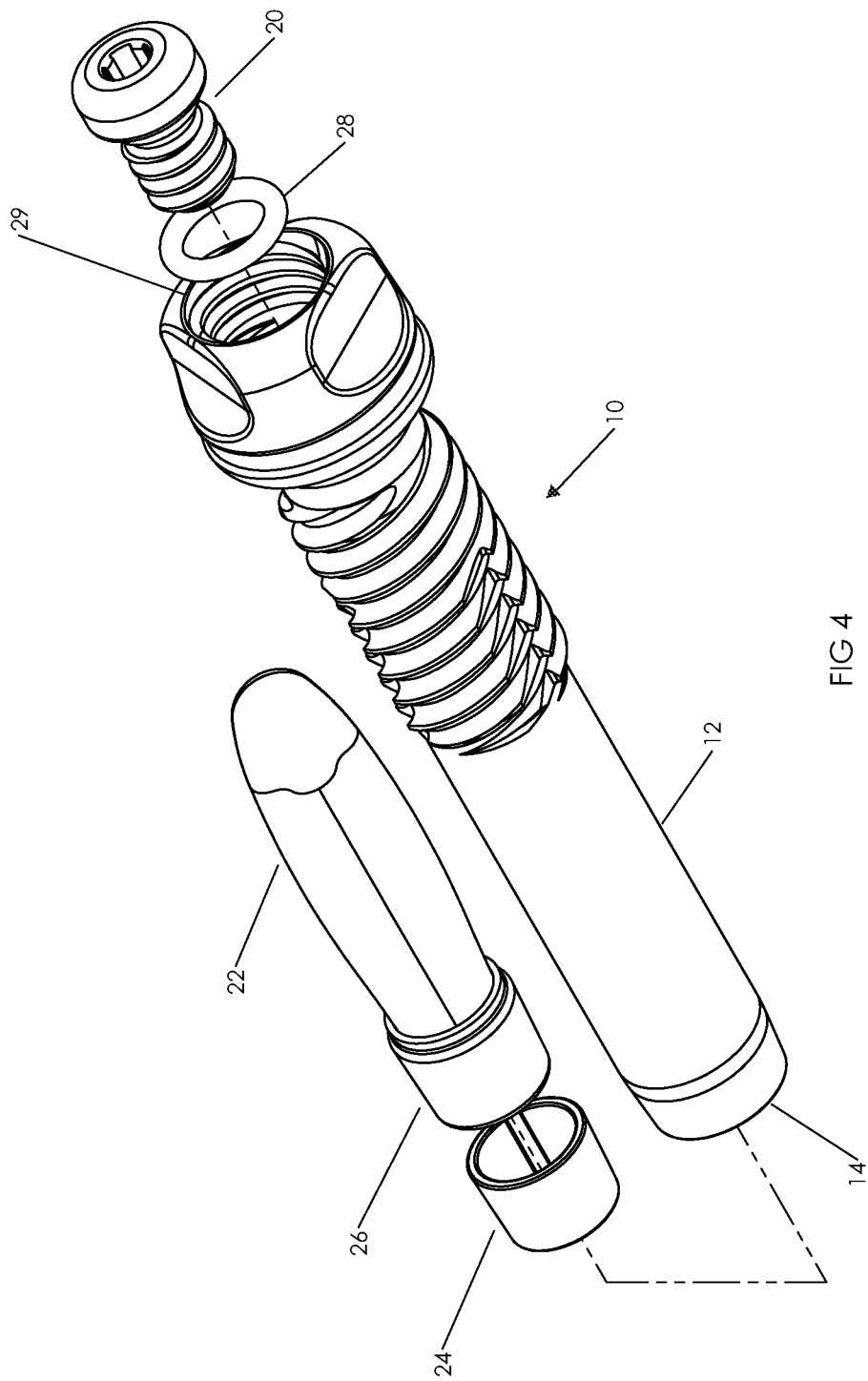
FIG. 4 is an exploded view thereof.
Figure 5:
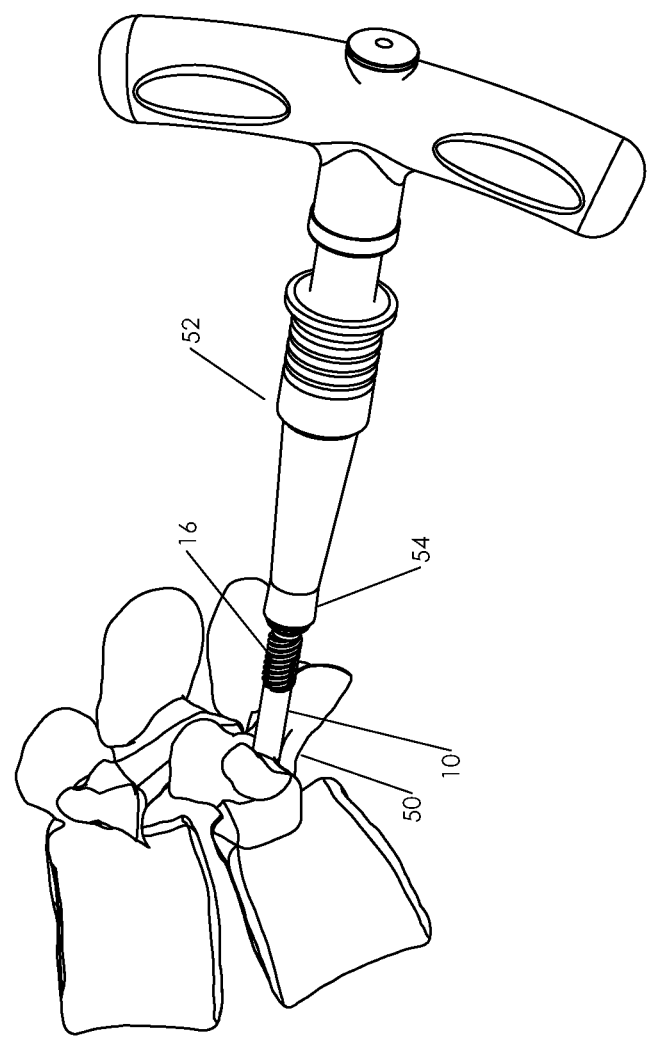
FIG. 5 is a pictorial view depicting the installation of the cannulated screw.

FIG. 4 depicts the cannulated screw 10 includes a hollow body 12 having an open end 14. An outer surface of the hollow body 12 is threaded along an upper portion 16 with a threaded cap 18 for receipt of a locking plug 20. The locking plug 20 may include an o-ring seal 28 to bias the locking plug in position and further provide for secondary sealing. The balloon 22 is shown separated from the hollow body 12, the balloon 22 is forced to pass through the ferrule 24 which is used in sealing the balloon 22 to the hollow body 12. Once the balloon 22 is filled with fluid, the locking plug 20 is threaded into the screw to secure the fluid within the balloon. The locking plug 20 may include an o-ring seal 28 to bias the locking plug 20 in position and further provide for secondary sealing, or the threads can be made of an interference fit for sealing.

Figure 6:
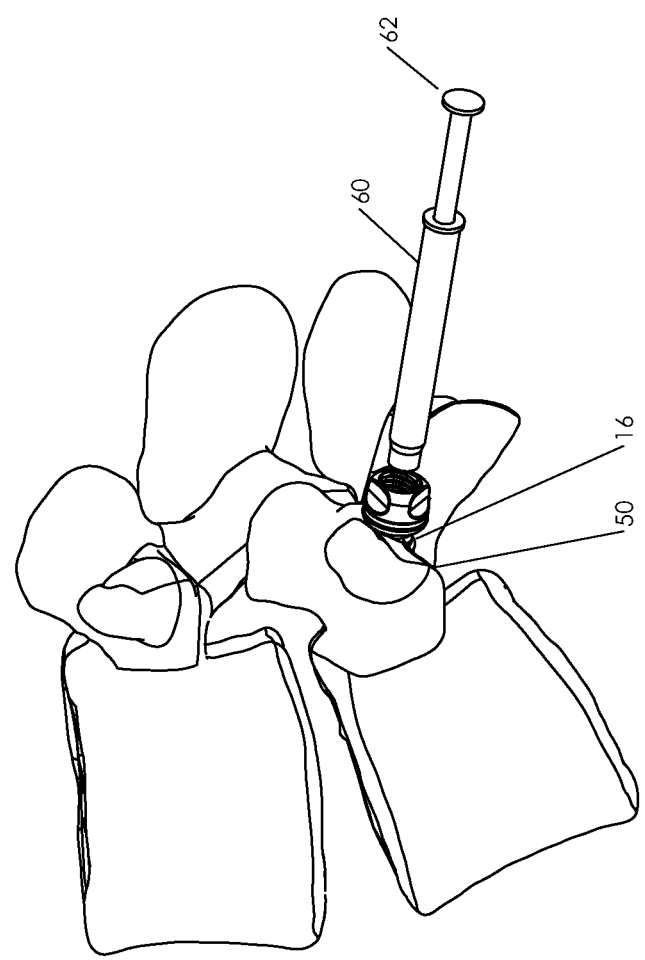
FIG. 6 is a pictorial view depicting the installation of the fluid injecting instrument.
Figure 7:
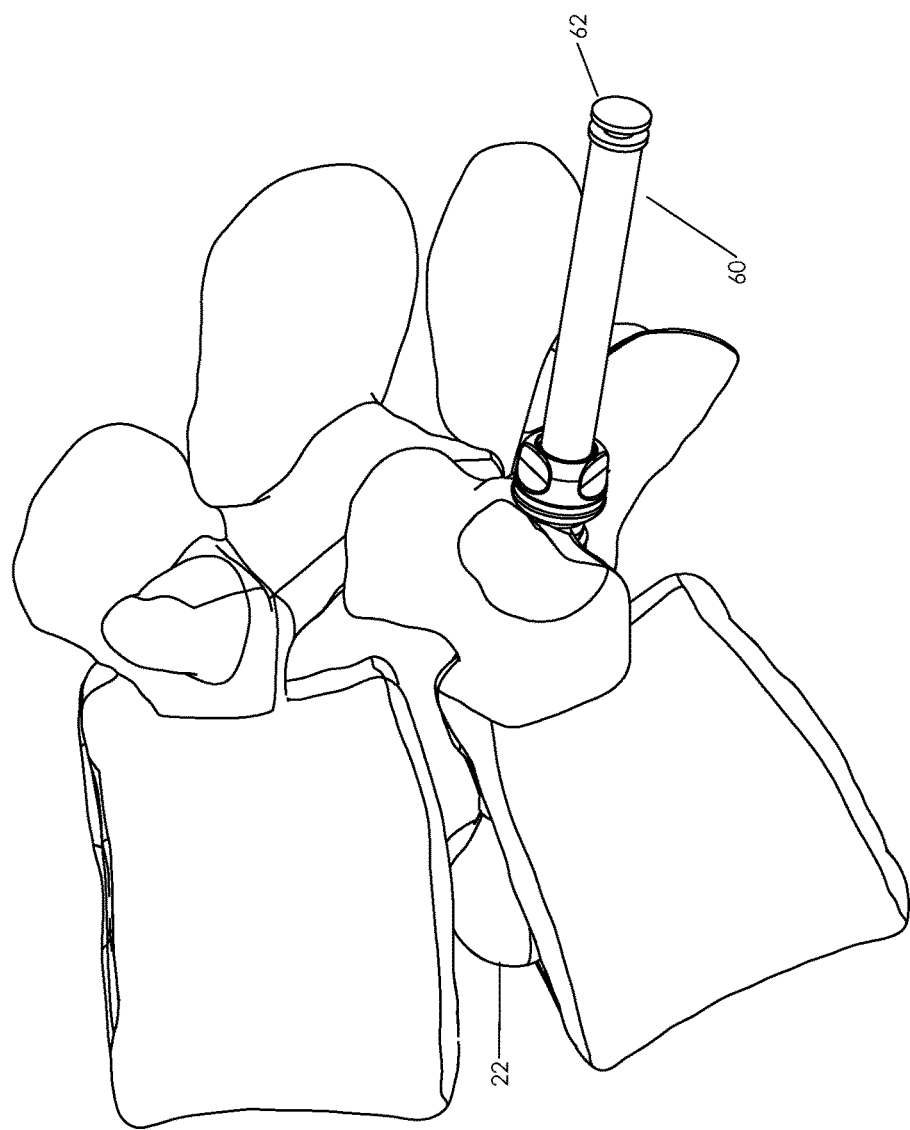
FIG. 7 is a pictorial view depicting the fluid injecting instrument mounted and expelled.

FIGS. 5-8 provide a pictorial view of the cannulated screw 10 placed through a pedicle 50 with an installation tool 52, the tool having a driver end 54 for engaging the threaded cap. It should be noted that any shape threaded cap may be used and considered within the scope of this invention. As shown in FIG. 6, the cannulated screw 10 is installed in the pedicle 50 with open second end 29 available for receipt of a volumetric material held in a dispenser 60. The dispenser 60 is coupled to the second end 29 and the volumetric material inserted by depressing of the carrier lever 62 filling the balloon 22 positioned between the intervertebral disc space. FIG. 8 is a further pictorial depicting a first and second cannulated screw 10 & 10' inserted into the vertebral body and exhibited balloons 22 & 22' filled with the volumetric material.

Suitable volumetric materials can be viscous and non-viscous including saline, gels, latex, polymers, polyethylenes, silicones, polyurethanes, metallics, ceramics, collagen, hydrogels. Volumetric materials can be radio-opaque contrast agents, allowing fluoroscopic viewing during injection into the disc to a known pressure.

The device can also be used to determine the excised nucleus pulposus weight and/or volumetric measurement of the tissue following removal. Corresponding amounts of nucleus replacement material are injected into the balloon 22 and a replacement for the nucleus can be determined.

Accordingly, in preferred embodiments, a transpedicular nucleus replacement device comprises a cannulated screw 10 having a hollow body 12 with an open first end 14 and an open second end 29, an expandable body 22 having an open end, a ferrule 24, a threaded cap 18, or a locking plug 20.

The expandable body extends upward into the hollow body from the open first end. The ferrule is inserted in the open end of the expandable body and forms a seal between the open first end of the cannulated screw and the expandable body. The second open end comprises threads for receiving a threaded cap, the threaded cap comprising threads for receiving a locking plug. In one preferred embodiment, the threaded cap comprises an O-ring seal. In another preferred embodiment, the locking plug comprises an O-ring seal. In another preferred embodiment, the threaded cap and locking plug comprise an O-ring seal.

In preferred embodiments, the balloon is fillable with fluids, filling biological agents or other material, the filling delivered to the expandable body from the open second end of the cannulated screw. In embodiments, the expandable body may be constructed from any of a variety of flexible materials, thereby enabling the expandable body to expand and contract to a variety of sizes.

In preferred embodiments, the cannulated screw comprises external threading, the external threading extending from about the second open end and extending for about one half to about a quarter of the length of the cannulated screw.

In other preferred embodiments, a cannulated screw comprises a hollow body, a first open end for receiving an expandable body, a second open end for receiving a threaded cap, the threaded cap comprising threads for receiving a locking plug. In embodiments, the threaded cap and/or the locking plug further comprise an O-ring seal.

In a preferred embodiment, the cannulated screw further comprises an expandable body receivable through the first open end, wherein the ferrule is fitted within the open end of the expandable body and provides a removable seal between the expandable body and the hollow body of the cannulated screw. In preferred embodiments, the expandable body is fillable with fluids, filling biological agents or other material, the filling delivered to the expandable body from the open second end of the cannulated screw.

In some embodiments, the second end optionally comprises a terminal end having a diameter wider than the hollow body for receiving the threaded cap. In other embodiments, the threaded cap is part of the cannulated screw.

In another preferred embodiment, the cannulated screw comprises external threading, the external threading extending from about the second open end and extending for about one half to about a quarter of the length of the cannulated screw.

In other embodiments, the device functions as an artificial disc prosthesis. In preferred embodiments, the device is manufactured from biocompatible components.

It is noted that the medical device described herein may be used for percutaneous pedicle access, as well as vertebroplasty and kyphoplasty surgeries.

In preferred embodiments, a method of treating a patient requiring an implantable spinal device, comprises surgically implanting the spinal device wherein the device comprises a cannulated screw having external threading for maintaining the position of the device once it has been implanted. The hollow body comprises an open first end for receiving a balloon, wherein the balloon extends upward into the hollow body from the open first end; a ferrule provides a seal between the balloon and hollow body; an open second end for receiving a threaded cap, the threaded cap comprising threads for receiving a locking plug. Once the device is implanted, the balloon is fillable with fluids, the ferrule providing a tight seal between the balloon and the hollow body, filling biological agents or other material, the filling delivered to the balloon from the open second end of the cannulated screw. The second end is then sealed with the tightening of the threaded cap and a locking plug which may comprise an O-ring seal.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A transpedicular nucleus replacement device comprising a cannulated screw having a hollow body with an open first end and an open second end, an expandable body secured to said open first end with a ferrule element, said expandable body extending entirely into said hollow body when in a non deployed position and extending out of said hollow body when fluid is directed through said open second end causing expansion of said expandable body in a deployed position, a threaded cap attached to said open second end, said threaded cap having threads positioned along an inner surface, and a locking plug securable to said threaded cap, said locking plug maintaining fluid in said expandable body to maintain said expandable body in the deployed position.

2. The transpedicular nucleus replacement device of claim 1, wherein the ferrule is inserted in an open end of the expandable body forming a seal between said open first end of the hollow body and said expandable body.

3. The transpedicular nucleus replacement device of claim 1, wherein said open second end comprises threads for receiving said threaded cap, said threaded cap includes threads for temporarily receiving a dispenser for use in inserting fluid into said expandable body.

4. The transpedicular nucleus replacement device of claim 1, wherein the locking plug further comprises an O-ring seal.

5. The transpedicular nucleus replacement device of claim 1, wherein the fluid comprises a biological agent being delivered to said expandable body from said open second end of the hollow body.

6. The transpedicular nucleus replacement device of claim 1, wherein said expandable body is a balloon.

7. The transpedicular nucleus replacement device of claim 1, wherein the cannulated screw comprises external threading, the external threading extending from said open second end and extending for one half to a quarter of the length of the cannulated screw.

8. The transpedicular nucleus replacement device of claim 1, wherein said open second end comprises a terminal end having a diameter greater than the hollow body for receiving the locking plug.

* * * * *